US009829493B2

(12) United States Patent
Svoboda et al.

(10) Patent No.: US 9,829,493 B2
(45) Date of Patent: Nov. 28, 2017

(54) METHODS AND APPARATUS FOR ASSESSMENT OF RISK FOR JOINT INJURY

(71) Applicants: Steven J. Svoboda, West Point, NY (US); Kenneth L. Cameron, New Windsor, NY (US)

(72) Inventors: Steven J. Svoboda, West Point, NY (US); Kenneth L. Cameron, New Windsor, NY (US)

( * ) Notice: Subject to any disclaimer, the term of this patent is extended or adjusted under 35 U.S.C. 154(b) by 0 days.

(21) Appl. No.: 14/905,777

(22) PCT Filed: Jul. 15, 2014

(86) PCT No.: PCT/US2014/046745
§ 371 (c)(1),
(2) Date: Jan. 15, 2016

(87) PCT Pub. No.: WO2015/009754
PCT Pub. Date: Jan. 22, 2015

(65) Prior Publication Data
US 2016/0154008 A1    Jun. 2, 2016

Related U.S. Application Data

(60) Provisional application No. 61/846,468, filed on Jul. 15, 2013.

(51) Int. Cl.
*G01N 33/68* (2006.01)

(52) U.S. Cl.
CPC ..... *G01N 33/6887* (2013.01); *G01N 2800/10* (2013.01); *G01N 2800/50* (2013.01); *G01N 2800/52* (2013.01); *G01N 2800/60* (2013.01)

(58) Field of Classification Search
CPC .......... G01N 33/6887; G01N 2800/10; G01N 2800/50; G01N 2800/52; G01N 2800/60
See application file for complete search history.

(56) References Cited

U.S. PATENT DOCUMENTS

| 4,444,879 | A | * | 4/1984 | Foster | G01N 33/545 422/400 |
| 5,292,636 | A | * | 3/1994 | Kung | C07K 16/2812 435/34 |
| 2004/0132064 | A1 | * | 7/2004 | Poole | A61K 49/0004 435/6.14 |
| 2005/0124071 | A1 | | 6/2005 | Kraus | |
| 2007/0264673 | A1 | * | 11/2007 | Wild | G01N 33/564 435/7.21 |
| 2010/0239590 | A1 | * | 9/2010 | Bowman | C07K 16/244 424/145.1 |
| 2011/0218116 | A1 | | 9/2011 | Cook et al. | |
| 2012/0083423 | A1 | | 4/2012 | Auger et al. | |

FOREIGN PATENT DOCUMENTS

WO    WO 2012/061821 A1    5/2012

OTHER PUBLICATIONS

Van Der Vekiens et al., Human and equine cardiovascular endocrinology: beware to compare, Cardiovascular Endocrinology 2013, vol. 2, No. 4, pp. 67-76.*
Torzewski et al., Animal Models of C-Reactive Protein, Hindawl Publishing Corporation, Mediators of Inflammation, vol. 2014, Article ID 683598, 2014, pp. 1-7.*
Strongin, Laboratory Diagnosis of Viral Infections, Sensitivity, Specificity, and Predictive Value of Diagnostic Tests: Definitions and Clinical applications, Lennette, ed. Marcel Dekker, Inc. New York, pp. 211-219, 1992.*
International Search Report and Written Opinion issued in International Patent Application No. PCT/US2014/046745 dated Feb. 6, 2015.
Verstappen S.M.M et al., Radiographic joint damage in rheumatoid arthritis is associated with differences in cartilage turnover and can be predicted by serum biomakers: an evaluation from 1 to 4 years after diagnosis, Arthritus research & therapy, 2006, vol. 8.1, pp. 1-9.

* cited by examiner

*Primary Examiner* — Gary W Counts
(74) *Attorney, Agent, or Firm* — Arent Fox LLP

(57) ABSTRACT

Test kits and methods for diagnosing and monitoring relative risk of joint injury are provided. The apparatus and methods beneficially permit intervention to reduce the risk of joint injury and/or reduce the damage resulting from joint injury. Methods for monitoring recovery from a joint injury are also provided.

14 Claims, 7 Drawing Sheets

Figure 6

Comparison of pre-injury mean serum biomarker concentrations between ACL injured cases and uninjured controls matched for sex, age, height, and weight.

|       | Control (n=45) | ACL Injury (n=45) | Matched-Pairs Difference (p-value) |
|-------|---------------|-------------------|-----------------------------------|
|       | mean (sd)     | mean (sd)         |                                   |
| C1,2C | 4.98 (0.53)   | 5.50 (0.55)       | <0.001                            |
| CPII  | 4.88 (0.54)   | 5.54 (0.54)       | <0.001                            |
| C2C   | 4.54 (0.54)   | 5.10 (0.57)       | <0.001                            |
| CS846 | 6.28 (0.38)   | 6.11 (0.43)       | 0.065                             |

Figure 7

Univariate and multivariable conditional logistic regression models evaluating the association between pre-injury serum biomarkers of cartilage turnover and subsequent ACL injury.

|  | Univariate | | | Final Multivariable Model[‡] | | |
|---|---|---|---|---|---|---|
|  | OR[†] | P | 95% CI | OR[†] | P | 95% CI |
| C1,2C | 9.12 | 0.001 | 2.55, 32.63 |  |  |  |
| C2C | 4.22 | 0.002 | 1.70, 10.45 | 3.38 | 0.049 | 1.01, 11.33 |
| CPII | 19.43 | 0.001 | 3.50, 107.82 | 28.09 | 0.004 | 2.97, 265.62 |
| CS846 | 0.35 | 0.080 | 0.11, 1.13 | 0.22 | 0.083 | 0.04, 1.22 |

[†]The uninjured control group matched for sex, age, height, and weight is the referent group.

[‡]Adjusted for sex, age, height, weight, and the other serum biomarkers in the model.

METHODS AND APPARATUS FOR ASSESSMENT OF RISK FOR JOINT INJURY

CROSS REFERENCE TO RELATED APPLICATION

This application is a 35 U.S.C. 371 National Phase of PCT Application No. PCT/US2014/046745 filed Jul. 15, 2014, which claims priority to U.S. Application No. 61/846,468 filed Jul. 15, 2013, the disclosure of each of which is hereby incorporated by reference in its entirety.

BACKGROUND OF THE INVENTION

1. Field of the Invention

The present invention relates generally to assessment of the relative risk of injury to joints. Test kits and methods for diagnosing and monitoring the relative risk of joint injury are provided. The apparatus and methods beneficially permit targeted intervention to reduce the risk of joint injury and/or reduce the damage resulting from joint injury.

2. Description of the Related Art

Joint injuries, such as sprains, strains, ligament tears, and degeneration of cartilage, may be chronic (i.e., occur as a result of aging, lack of use, or overuse), or acute (i.e., occur as a result of accident or trauma). Combinations of these factors may work together to contribute to joint injuries.

Biomechanical movement and neuromuscular risk factors associated with joint injury have recently begun to emerge, particularly with respect to injury to the anterior cruciate ligament (ACL) (6). High risk biomechanical movement patterns can result in the transmission of ground reaction forces to the knee, which in turn increase the compressive forces in the joint (7). Specifically, frontal plane motions, such as excessive knee abduction angle during landing maneuvers, may result in increased axial compression that can lead to traumatic ACL rupture (11). Hewett et al. (23) demonstrated that landing with excessive knee abduction is a prospective risk factor for subsequent ACL injury. It has been suggested that abnormal joint loading during activity may also accelerate the initiation and progression of osteoarthritis, particularly in the knee (16, 17, 44).

Despite the promising data that suggest certain high risk movement patterns may predispose individuals to joint injury, little is known about how these movement patterns might affect biochemical processes associated with cartilage, bone, muscle, ligament, and tendon metabolism. More specifically, little is known about how pre-injury cartilage turnover and metabolism are associated with subsequent joint injury.

Efforts to use biomarkers to predict the onset of osteoarthritis are underway. Since ACL injuries may lead to arthritis, an area of research has evolved around studying the earliest stages of arthritis that may occur following major knee joint injuries, such as ACL tears, by using biomarkers. For example, U.S. Published Patent Application No. 2011/0218116 describes biomarkers and methods for diagnosing osteoarthritis, based on measurement of the expression of polypeptides including MCP1, IL8, KC, MMP2, MMP3, IL6, MMP1, RANTES, MMP9, IL1B, Apolipoprotein A1, Apolipoprotein E, DCN, CILP and COMP.

However, such methods of using biomarkers assess the impact of joint injuries only after they have occurred, and do not permit a determination of those at risk for such injuries. Accordingly, there remains a need in the art for tools and methods for assessing the risk of joint injury.

SUMMARY OF THE INVENTION

The present invention meets the unmet needs of the art, as well as others, by providing test kits and methods for assessing the risk of injury to joints. The test kits and methods may be used for diagnosing and monitoring risk of joint injury. The test kits and methods may also be used to reduce the risk of joint injury and/or reduce the damage resulting from joint injury in persons determined to be at risk.

According to one aspect of the invention, methods for assessing an elevated risk of future injury to a joint are provided. The methods include comparing expression of one or more biomarkers of cartilage, bone, muscle, ligament, and tendon metabolism in a subject suspected of having an elevated risk of joint injury, with the expression of said same one or more biomarkers in a control subject not suspected of having an elevated risk of joint injury. The biomarkers may be selected from the group consisting of C1,2C, C2C, CPII, and CS846, CTX-II, COMP, HA, Coll2-1 and Coll2-1NO2, PHANP, NTX-1, CTX-1, MMP1-MMP3, MMP7-MMP28, VEGF, PDGF, IGF-1, IGF-2, CRP, ESR, and Vitamin D. The subject suspected of having an elevated risk of joint injury is identified based on biochemical assessment of cartilage turnover and joint metabolism, and optionally a biomechanical assessment of joint movement. The joint may be selected from the group consisting of foot, ankle, hip, hand, wrist, elbow, shoulder, and neck, and the joint injury may be selected from the group consisting of tears, stretching, and irritation of tendons and ligaments, dislocation of joints, and damage and wearing of cartilage. In accordance with some embodiments, the joint is a knee, and the injury to the joint is an ACL tear.

An additional aspect of the invention relates to methods for monitoring recovery from a joint injury. The methods involve conducting ongoing assessment of expression of one or more biomarkers of cartilage, bone, muscle, ligament, and tendon metabolism in a subject having suffered from a joint injury, and comparing the expression of said same one or more biomarkers in the subject having suffered from a joint injury with previously-obtained expression levels said subject who suffered from a joint injury. Biomechanical assessments may also be used to monitor improvement of joint recovery.

Another aspect of the invention relates to methods for reducing the risk of joint injury. The methods include assessing risk of future injury to a joint by comparing expression of one or more biomarkers of cartilage, bone, muscle, ligament, and tendon metabolism in a subject suspected of having an elevated risk of joint injury, with the expression of said same one or more biomarkers in a control subject not suspected of having an elevated risk of joint injury, and providing physical therapy and/or movement retraining interventions to said subject suspected of having an elevated risk of joint injury to correct defects in movement of joints.

Another aspect of the invention relates to methods for determining an elevated risk of injury to a joint in a subject suspected of having an elevated risk of joint injury, including (a) providing a sample obtained from a subject; (b) assessing the expression level of two or more biomarkers of cartilage metabolism in the sample taken from the subject; (c) comparing the expression level of the two or more biomarkers in the sample with the expression level of the same two or more biomarkers in a normal control; and (d) determining whether the subject has an elevated risk of future injury to a joint based on the result of step (c). The methods may further encompass conducting a biomechanical assessment of the joint. The methods may further encompass administering an intervention to the subject to reduce the elevated risk of future injury to a joint. The intervention may be selected from the group consisting of physical therapy, movement retraining, surgery, and pharmaceutical therapy. The methods may also be incorporated into methods for diagnosing and reducing an elevated risk of injury to a joint, and monitoring treatment of subjects having an elevated risk of joint injury.

Another aspect of the invention relates to methods for determining an elevated risk of future injury to a joint in a subject suspected of having an elevated risk of joint injury, including (a) providing a sample obtained from a subject; (b) assessing the protein expression level of two or more biomarkers of cartilage metabolism in the sample taken from a subject suspected of having an elevated risk of joint injury, said biomarkers selected from the group consisting of C1,2C, C2C, CPII, and CS846; (c) comparing the protein expression level of the two or more biomarkers in the sample with the protein expression level of the same two or more biomarkers in a normal control; and (d) determining whether the subject has an elevated risk of future injury to a joint in accordance with the result of step (c); wherein protein expression levels of C1,2C, C2C, or CPU in the sample that are higher than those in the normal control indicate an elevated risk of future injury to a joint, and protein expression levels of CS846 in the sample that are lower than those in the normal control indicate elevated risk of future injury to a joint. The methods may further encompass administering an intervention to the subject to reduce the elevated risk of future injury to a joint. The intervention may be selected from the group consisting of physical therapy, movement retraining, surgery, and pharmaceutical therapy.

Another aspect of the invention relates to methods for diagnosing and reducing an elevated risk of future injury to a joint, including (a) providing a sample obtained from a subject; (b) assessing the expression level of one or more biomarkers of cartilage metabolism in the sample taken from a subject suspected of having an elevated risk of joint injury, said biomarkers selected from the group consisting of C1,2C, C2C, CPII, and CS846; (c) comparing the expression level of the one or more biomarkers in the sample with the expression level of the same one or more biomarkers in a normal control; (d) determining that the subject has an elevated risk of future injury to a joint based on expression levels of C1,2C, C2C, or CPII in the sample that are higher than those in the normal control or expression levels of CS846 in the sample that are lower than those in the normal control; and (e) administering a joint-injury reducing intervention to the diagnosed subject to reduce the elevated risk of future injury to a joint.

Another aspect of the invention relates to methods for monitoring treatment of a subject having an elevated risk of future injury to a joint, including (a) providing a first sample obtained from the subject being treated at a first time; (b) assessing the expression level of one or more biomarkers of cartilage metabolism in the first sample, said biomarkers selected from the group consisting of C1,2C, C2C, CPII, and CS846; (c) providing a second sample obtained from the subject being treated at a second time later than said first time; (d) assessing the expression level of the same one or more biomarkers of cartilage metabolism in the second sample, said biomarkers selected from the group consisting of C1,2C, C2C, CPII, and CS846; and (e) comparing the expression level of the one or more biomarkers in the first sample with the expression level of the same one or more biomarkers in the second sample. The methods further include either (f)(1) determining that the treatment of the subject having an elevated risk of future injury to a joint is effective based on expression levels of at least one of C1,2C, C2C, or CPII in the second sample that are lower than those in the first sample, or expression levels of CS846 in the second sample that are higher than those in the first sample, or (f)(2) determining that the treatment of the subject having an elevated risk of future injury to a joint is not effective based on expression levels of at least one of C1,2C, C2C, or CPII in the second sample that are the same as or greater than those in the first sample, or expression levels of CS846 in the second sample that are lower than those in the first sample.

Another aspect of the invention relates to methods for diagnosing an elevated risk of future injury to a joint in a subject by analyzing a sample from said subject for increased cartilage turnover, wherein the subject has an elevated risk of future injury to a joint if increased cartilage turnover is detected.

Another aspect of the invention relates to methods for diagnosing and reducing an elevated risk of joint injury in a subject by analyzing a sample from said subject for the presence or absence of one or more biomarkers selected from the group consisting of C1,2C, C2C, CPII, and CS846, wherein the subject is diagnosed with an elevated risk of joint injury if elevated levels of C1,2C, C2C, or CPII are detected, or if decreased levels of CS846 are detected; and administering a joint-injury reducing intervention to the diagnosed subject.

Another aspect of the invention relates to methods for diagnosing an elevated risk of joint injury in a subject, wherein the elevated risk of joint injury is characterized by increased levels relative to a control of a biomarker selected from the group consisting of C1,2C, C2C, and CPII, or by decreased levels relative to a control of a biomarker CS846, including i) obtaining a biological sample from the subject; ii) applying a reagent specific for the biomarker to the sample, wherein presence of the biomarker creates a reagent-biomarker complex; iii) applying a detection agent that detects the reagent-biomarker complex; iv) comparing the amount of reagent-biomarker complex in the sample relative to the control; and v) diagnosing an elevated risk of joint injury based on the comparison of the amount of reagent-biomarker complex in the sample as compared to the control. The methods may further include providing one or more interventions to reduce the risk of joint injury.

According to a further aspect, the invention relates to test kits for carrying out the methods that include reagents for detecting the one or more biomarkers, and a control.

Other novel features and advantages of the present invention will become apparent to those skilled in the art upon examination of the following or upon learning by practice of the invention.

BRIEF DESCRIPTION OF THE DRAWINGS

FIG. 6 is a table comparing pre-injury serum biomarker levels between ACL injured cases and uninjured controls matched for sex, age, height, and weight.

FIG. 7 includes univariate and multivariable conditional logistic regression models evaluating the association between pre-injury serum biomarkers of cartilage turnover and subsequent ACL injury.

DETAILED DESCRIPTION OF THE INVENTION

Figure 1:
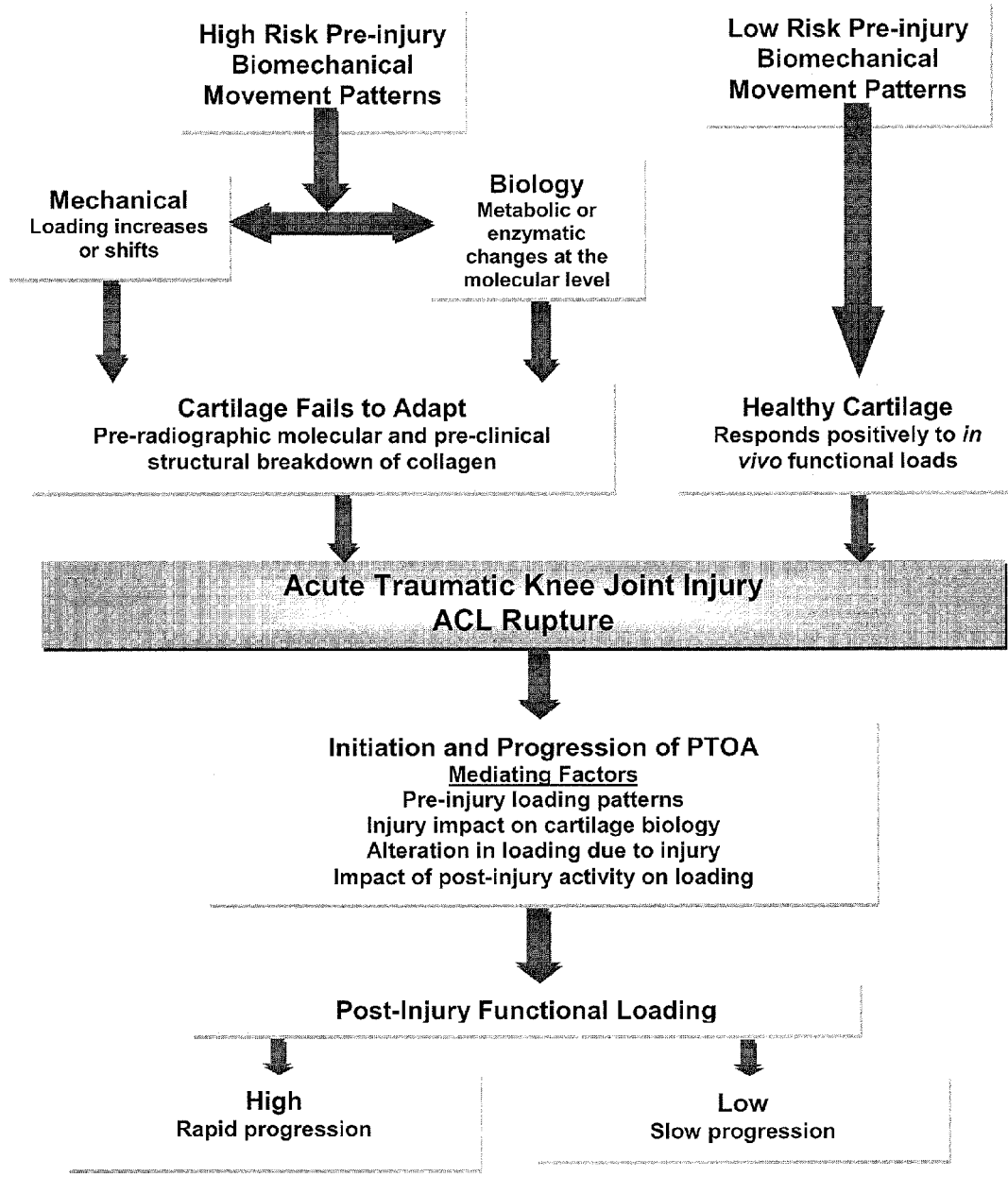
FIG. 1 is a flowchart providing a conceptual framework for the in vivo pathomechanics of post-traumatic osteoarthritis (PTOA) (adapted from: Andriacchi T P, Mundermann A. The role of ambulatory mechanics in the initiation and progression of knee osteoarthritis. *Curr Opin Rheumatol.* 2006; 18:514-518).
Figure 2:
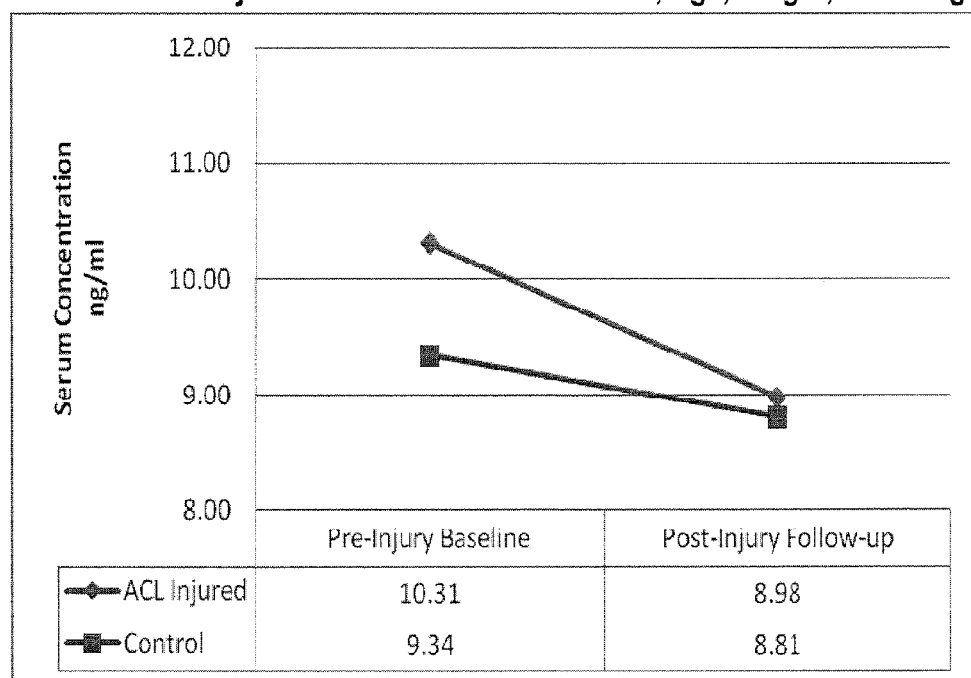
FIG. 2 is a graph depicting the change in median serum C2C concentration over time for subjects with ACL injuries vs. uninjured controls.
Figure 3:
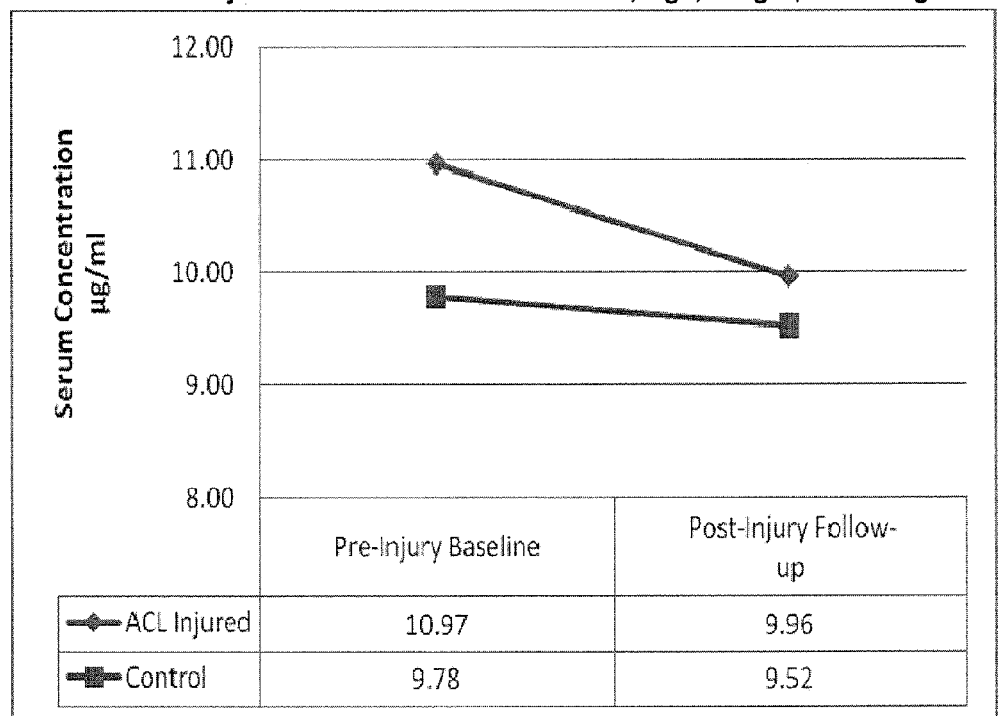
FIG. 3 is a graph depicting the change in median serum C1,2C concentration over time for subjects with ACL injuries vs. uninjured controls.
Figure 4:
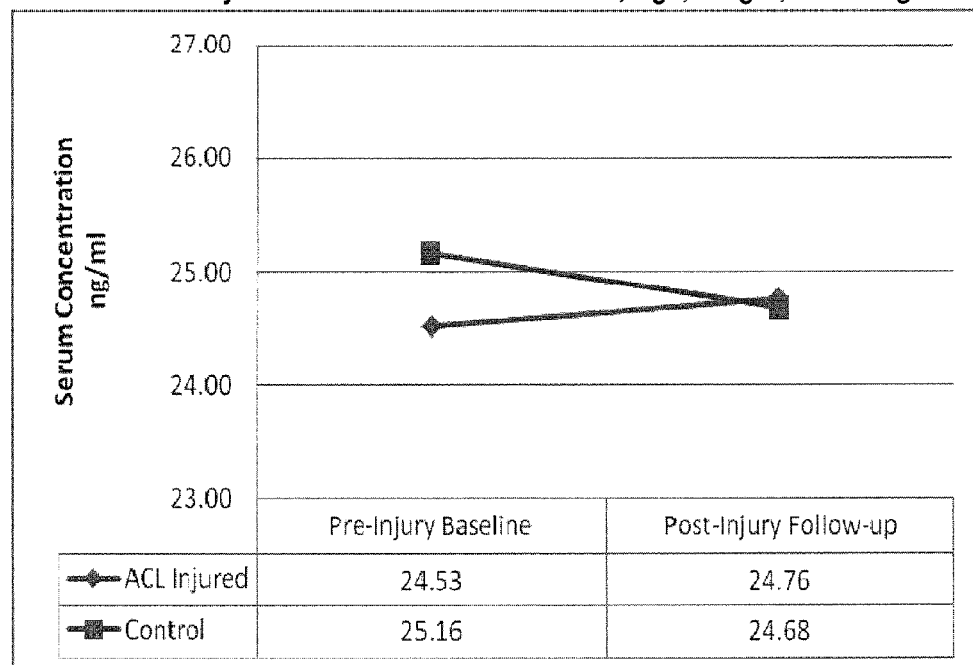
FIG. 4 is a graph depicting the change in median serum CS846 concentration over time for subjects with ACL injuries vs. uninjured controls.
Figure 5:
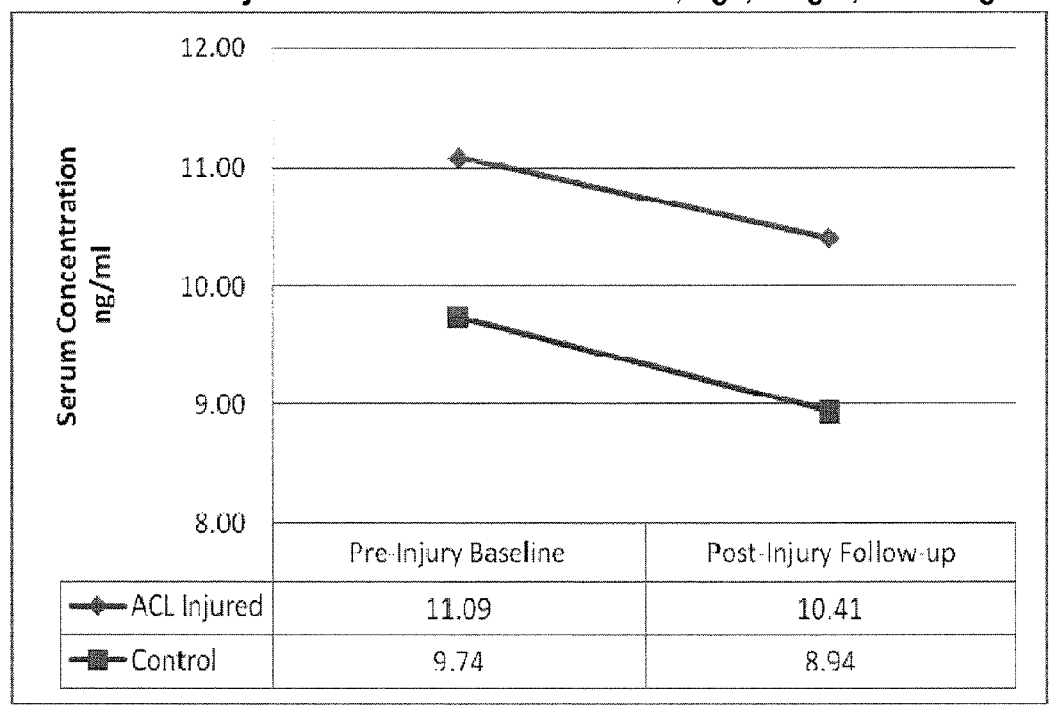
FIG. 5 is a graph depicting the change in median serum CPII concentration over time for subjects with ACL injuries vs. uninjured controls.

The present invention relates generally to assessment of the risk of injury to joints. Test kits and methods for diagnosing and monitoring risk of joint injury using biomarkers are provided. The apparatus and methods beneficially permit intervention to reduce the risk of joint injury (primary prevention) and/or reduce the damage resulting from joint injury in the future (secondary prevention).

The methods described herein, and the diagnostic reagents, kits and related inventions disclosed herein, are based in part on the surprising discovery of a plurality of biomarkers, the expression levels of which consistently differentiate between normal, healthy subjects having a low risk of future joint injury and subjects with a high risk of future joint injury.

The risk profile determined using the plurality of biomarkers may be supplemented with biomechanical information derived from further testing of the subject to provide additional risk assessment capability. These biomechanical assessments or tests may include, but are not limited to, administration of the Landing Error Scoring System (LESS) developed by the Sports Medicine Research Laboratory at the University of North Carolina (UNC), Chapel Hill; three-dimensional motion analyses with integrated ground reaction force assessments during gait or a jump landing task; and assessments of isometric strength of muscles surrounding the joints. LESS is a system with scoring of a zero (0), one (1), and sometimes two (2), corresponding to the presence or absence of specific findings. The subject jumps forward from a standard plyometric box (having a height of approximately 30 cm) using both feet, over a standard distance equal to half the subject's body height. After landing on both feet, the subject jumps vertically for maximal height, and upon landing from the maximal height jump, the landing is assessed using multiple criteria. Assessment may be conducted with or without a video recording of the jumps. The assessment criteria include analysis of both side and frontal characteristics. Side view criteria include: hip flexion angle at contact—hips are flexed (Yes=0, No=1); trunk flexion angle at contact—trunk in front of hips (Yes=0, No=1); knee flexion angle at contact—greater than 30 degrees (Yes=0, No=1); ankle plantar flexion angle at contact—toe to heel (Yes=0, No=1); hip flexion at max knee flexion angle—greater than at contact (Yes=0, No=1); trunk flexion at max knee flexion—trunk in front of the hips (Yes=0, No=1); knee flexion displacement—greater than 30 degrees (Yes=0, No=1); sagittal plane joint displacement (Large motion (soft)=0, Average=1, Small motion (loud/stiff)=2). Frontal view criteria include: lateral (side) trunk flexion at contact—trunk is flexed (Yes=0, No=1); knee valgus angle at contact—knees over the midfoot (Yes=0, No=1); knee valgus displacement—knees inside of large toe (Yes=1, No=0); foot position at contact—toes pointing out greater than 30 degrees (Yes=1, No=0); foot position at contact—toes pointing out less than 30 degrees (Yes=1, No=0); stance width at contact—less than shoulder width (Yes=1, No=0); stance width at contact—greater than shoulder width (Yes=1, No=0); initial foot contact—symmetric (Yes=0, No=1); overall impression (Excellent=0, Average=1, Poor=2). The LESS scale rates subjects' biomechanical performance as follows: excellent (0-3); good (4-5); moderate (6); or poor (7 or greater).

The biomarkers are proteins produced through various biological processes in a subject, as measured from a biological sample obtained from the subject, which are indicative of the risk of joint injury in the subject. Also provided herein are methods of using the biomarkers to identify a candidate substance as a therapeutic substance for preventing joint injury, methods of using the biomarkers to determine the efficacy of a physical therapy and/or movement retraining program in training a subject at risk of joint injury to adopt a movement profile that results in a lower risk of joint injury, and diagnostic reagents and kits for monitoring and/or testing a subject's risk of joint injury.

The methods of the invention may combine the detection of biomarkers with biomechanical movement assessments for the assessment of risk of an ACL injury, the primary prevention of ACL and other joint injury, as well as the primary and secondary prevention of degenerative joint disease in those with high risk movement profiles. The biomarkers may include, but are not limited to, C1,2C, C2C, CPII, CS846, CTX-II, COMP, HA, Coll2-1 and Coll2-1NO2, PHANP, NTX-1, CTX-1, MMP1-MMP3, MMP7-MMP28, VEGF, PDGF, IGF-1, IGF-2, CRP, ESR, and Vitamin D. The assessments may include administration of the Landing Error Scoring System (LESS), and three dimensional motion analyses with integrated ground reaction force assessments during gait or a jump landing or cutting/changing direction task.

In addition to providing methods for the primary prevention of ACL injury, the methods may be used in accordance with methods for determining the risk of injury to other ligaments, cartilage, or meniscus of the knee.

The methods of the invention may also be utilized to determine the risk of injury to other weight-bearing joints, and to predict the risk of osteoarthritis to any joint or specific joints in an individual in the future, by detecting expression levels of one or more biomarkers of cartilage, bone, muscle, ligament, and tendon metabolism in a subject. Prediction of the risk of osteoarthritis of the knee is a particular focus of these methods.

The invention also encompasses methods and apparatus for minimizing the risk of joint injury, and methods for measuring individual responses to such potential injury risk prevention methods and apparatus. The intervention may be selected from the group consisting of physical therapy, movement retraining (e.g., to improve biomechanical form), surgery (e.g., correcting physical defects in a joint that result from prior injury, overuse, and/or structural abnormality), apparatus (e.g., braces or supports), and pharmaceutical therapy (e.g., administering one or more compositions to improve joint health and/or reduce inflammation in the joints). These methods also include comparing the expression of one or more biomarkers in a subject after receiving an intervention to minimize the risk of joint injury, with the expression of said same one or more biomarkers in said subject prior to initiation of the risk prevention methods or use of the apparatus for minimizing risk of joint injury. Based on this comparison a determination of the effectiveness of the intervention may be made.

Without wishing to be bound by theory, it is theorized that high risk biomechanical movement profiles that place individuals at increased risk for joint injury may also influence cartilage turnover and metabolism prior to injury. The biochemical events induced by biomechanical forces during movement may, over time, destabilize the normal metabolic processes associated with cartilage synthesis and degradation, also referred to as cartilage turnover (2, 36). It is theorized that movement characteristics may influence to what degree joint cartilage fragments escape from the joint due to an overall increase in loads seen by the joint in persons with these movement profiles. This may be particularly true in individuals with high risk movement patterns, as set forth in FIG. 1 and described in greater detail below. If individuals are at increased risk of joint injury due to high risk biomechanical movement patterns, particularly those that increase compressive forces at the joint, these movement patterns may also alter cartilage turnover and metabolism prior to injury, for example, by increasing cartilage turnover and metabolism.

The apparatus, test kits, and methods described herein are applicable to any type of joint injury, however, in view of the high frequency of knee injuries and the difficulty in recovering therefrom, they are considered particularly useful for predicting elevated risk of knee injury. One common knee injury that may be predicted and/or prevented using the test kits and methods of the invention are ACL tears. Injuries involving the ligaments, menisci, articular cartilage, and bone of other joints are also within the scope of the invention, which includes, but is not limited to, injuries to the foot, ankle (e.g., Achilles tendon), hip, hand, wrist, elbow, shoulder (e.g., glenoid labrum and capsule) and neck. The joint injuries that may be predicted and/or prevented encompass tears, stretching, and irritation of tendons and ligaments, dislocation of joints, and damage and wearing of menisci, articular cartilage, and bone.

According to one aspect, the test kits and methods of the invention may be used to predict future joint injury using commercially-available enzyme linked immunosorbent assays (ELISAs) to measure biomarkers in the blood and apply the resulting biomarker concentrations along with measurable movement characteristics in a novel manner to predict risk for joint injury. However, radioimmunoassay and other immunoassay technologies may be used in accordance with the invention. Additional detection methods may also be employed in order to identify biomarkers, including PCR. Various techniques for the detection of the biomarkers may be accomplished using techniques that are well known to those skilled in the art, for example, those described in Ausubel et al., (2003) CURRENT PROTOCOLS IN MOLECULAR BIOLOGY, John Wiley & Sons, New York, N.Y., or Sambrook et al. (1989) MOLECULAR CLONING: A LABORATORY MANUAL, Cold Spring Harbor Press, Cold Spring Harbor, N.Y.

The biomarkers that may be used in accordance with the test kits and methods of the presently-claimed invention encompass any protein, polypeptide, polynucleotide, antibody, or fragment thereof. The biomarker may be present in a test sample from a subject, and have an expression level that has been found to be indicative of the risk of a future joint injury in the subject as described herein. The biomarkers may be used alone, or in conjunction with other markers, such as visual markers obtained, for example, using MRI, ultrasound, arthroscopy, PET, CT, PET-CT, and x-ray images. The biomarkers may also be used in conjunction with biomechanical information obtained through physical evaluation and assessment of the movement patterns of a subject. These tests may include administration of the Landing Error Scoring System (LESS) and three dimensional motion analyses with integrated ground reaction force assessments during gait or a jump landing task designed to assess angle, speed, and rotation of joints observed during specific movements (kinematics), and measurements of forces exerted during specific movements (kinetics). Assessment of isometric strength of muscles may be incorporated into the biomechanical assessment, where such measurements may be made, for example, using a dynamometer.

Particular biomarkers having predictive value for future joint injury may include, but are not limited to C1,2C, C2C, CPII, and CS846. These markers may be detected in any suitable body fluid, and may be detected in some aspects from serum and urine. C1,2C is a marker of cartilage metabolism that is generated by the cleavage of type I (bone) and type II (cartilage) collagen by collagenases. C2C is a marker of type II (cartilage) collagen degradation. CPII is a marker that measures the rate of synthesis of collagen and measures a carboxy propeptide that is released when procollagen is cleaved to form collagen. CS846 is a marker for changes in the rate of synthesis of the cartilage component aggrecan, where the aggrecan that is measured has been released from cartilage following cleavage by matrix metalloproteinase and/or aggrecanase enzymes. This is thought to occur when the body attempts to repair damage in adult cartilage.

FIGS. 2-5 provide comparisons of representative levels of these markers in subjects considered to be at risk of future joint injury based on prior incidence of ACL injury, as compared to subjects not considered to be at risk of future joint injury based on absence of prior incidence of ACL injury. These biomarkers are primarily focused on collagen metabolism, but additional biomarkers relevant to joint damage may include markers for bone metabolism, muscle metabolism, ligament metabolism, and tendon metabolism, and these additional biomarkers may be detected in lieu of or in addition to the detection of C1,2C, C2C, CPII, and CS846. These may include, but are not limited to, CTX-II (which may be detected, e.g., in urine), COMP (which may be detected, e.g., in serum), HA (which may be detected, e.g., in serum), Coll2-1 and Coll2-1, NO2 (which may be detected, e.g., in serum and/or urine), PHANP, NTX-1 (which may be detected, e.g., in serum and/or urine), CTX-1 (which may be detected, e.g., in serum and/or urine), and MMP-3 (which may be detected, e.g., in serum). Further biomarkers include, MMP1, MMP2, MMP7-MMP28, VEGF, PDGF, IGF-1, IGF-2, CRP, ESR, and Vitamin D.

A biomarker having predictive value for future joint injury is indicative of future joint injury when the expression level or quantity or structure of the biomarker is found significantly more often in subjects who have an elevated risk of experiencing a future joint injury, than in subjects who are not at an elevated risk of experiencing a future joint injury. Significance of an expression level, quantity or structure of the biomarker, as compared to a control, is determined using routine statistical methods, such as by applying accepted confidence levels, e.g. at a minimum of 95%. Cut-off or threshold expression levels for each biomarker for elevated risk of future joint injury may be determined based on factors such as the degree of correlation of the expression level with clinical or subclinical indicators of joint injury. The expression level of a biomarker that is indicative of an elevated risk of future joint injury can be, for example, that found in at least 60% of patients who have an increased risk of experiencing a future joint injury and is found in less than 10% of subjects who do not have an elevated risk of experiencing a future joint injury. More preferably, an expression level is indicative of an elevated risk of future joint injury if it is found in at least 70%, at least 75%, at least 80%, at least 85%, at least 90%, at least 95%, at least 97%, at least 98%, at least 99% or more in subjects who have an elevated risk of experiencing a future joint injury and is found in less than 20%, less than 10%, less than 8%, less than 5%, less than 2.5%, or less than 1% of subjects who do not have an elevated risk of experiencing a future joint injury.

An elevated risk of future joint injury for purposes of the present invention is defined with the understanding that even a person considered to have a low level of risk of future joint injury may still experience a joint injury, for example, due to accident. The elevated risk of joint injury therefore encompasses an increased likelihood of experiencing a joint injury as compared to the level of risk of joint injury of a control subject not at an elevated risk of future joint injury.

With respect to the biomarkers C1,2C, C2C, and CPII, expression levels that are higher than those of control patients are associated with significant increases in risk of future joint injury. For example, expression levels that are from 0.25 to 2.5 ng/ml higher than in control patients are associated with significant increases in risk of future joint injury. Preferably, expression levels that are from 0.5 to 1.75 ng/ml higher than in control patients are associated with significant increases in risk of future joint injury. More preferably, expression levels that are from 0.75 to 1.25 ng/ml higher than in control patients are associated with significant increases in risk of future joint injury. Most preferably expression levels that are about 1 ng/ml higher than in control patients are associated with significant increases in risk of future joint injury.

With respect to the biomarker CS846, expression levels that are higher than those of control patients are associated with significant decreases in risk of future joint injury. For example, expression levels that are from 0.25 to 2.5 ng/ml higher than in control patients are associated with significant decreases in risk of future joint injury. Preferably, expression levels that are from 0.5 to 1.75 ng/ml higher than in control patients are associated with significant decreases in risk of future joint injury. More preferably, expression levels that are from 0.75 to 1.25 ng/ml higher than in control patients are associated with significant decreases in risk of future joint injury. Most preferably expression levels that are about 1 ng/ml higher than in control patients are associated with significant decreases in risk of future joint injury.

A subject is considered to be at an elevated risk of a future joint injury if the detected expression levels in the biomarkers of the subject deviate from the expression levels of those biomarkers in a control subject. The deviation of a particular biomarker relative to a control subject may be correlated with either an increased risk of future joint injury, or a reduced risk of future joint injury. For example, elevated expression of the biomarkers C1,2C, C2C, and CPII is associated with an increase in the likelihood of joint injury, while elevated expression of the biomarker CS846 is associated with a reduced likelihood of injury. Reduced expression of the biomarker CS846 is associated with an increased likelihood of injury. The increased risk of future joint injury may be an increase of about 50% or higher, preferably an increase of about 200% or higher, more preferably an increase of about 400% or higher, and most preferably an increase of about 800% or higher. The reduced risk of future joint injury may be a decrease of about 25% or more, preferably an increase of about 35% or higher, more preferably an increase of about 50% or higher, and most preferably an increase of about 65% or higher.

Any one of the biomarkers C1,2C, C2C, CPII, and CS846 may be measured in order to assess the increased risk of future joint injury. Preferably any combination of two or more of the biomarkers C1,2C, C2C, CPII, and CS846 may be measured in order to assess the increased risk of future joint injury. More preferably, any combination of three or more of the biomarkers C1,2C, C2C, CPII, and CS846 may be measured in order to assess the increased risk of future joint injury. Most preferably, the combination of C2C, CPII, and CS846 are measured in order to assess the increased risk of future joint injury. All four of the biomarkers C1,2C, C2C, CPII, and CS846 may also be measured in order to assess the increased risk of future joint injury.

It is also within the scope of the present invention to measure any of the above combinations of the biomarkers C1,2C, C2C, CPII, and CS846, along with one or more additional biomarkers for bone metabolism, muscle metabolism, ligament metabolism, and tendon metabolism, as well as in combination with information obtained from physical evaluation of the movement patterns of a subject, including angles of joints observed during specific movements, and measurements of forces exerted during specific movements, as well as joint imaging techniques such as MRI, ultrasound, bone scans, etc.

The biomarkers that may be measured in accordance with the invention can be obtained from any sample of a biological material that is suspected of containing an analyte of interest. Examples of biological materials that may be sources of samples for analysis include, but are not limited to, stool, whole blood, serum, plasma, red blood cells, platelets, interstitial fluid, saliva, ocular lens fluid, cerebral spinal fluid, sweat, urine, ascites fluid, mucous, nasal fluid, sputum, synovial fluid, peritoneal fluid, vaginal fluid, menses, amniotic fluid, semen, etc. Preferably, the test sample is a serum or urine sample. The test sample may be used directly as obtained or following a pretreatment to modify the sample. For example, pretreatment may include preparing plasma or serum from blood. Methods of pretreatment may also involve filtration, precipitation, dilution, distillation, mixing, concentration, inactivation of interfering components, the addition of reagents, lysing, etc. If such methods of pretreatment are employed with respect to the test sample, such pretreatment methods are such that the analyte of interest remains in the test sample at a concentration proportional to that in an untreated test sample (e.g., a test sample that is not subjected to any such pretreatment method(s)).

In order to assist in monitoring recovery, assessment of expression of one or more biomarkers of cartilage, bone, muscle, ligament, and tendon metabolism in the subject having suffered from a joint injury may be conducted at regular intervals (e.g., once per week, once per month, once per quarter). The expression is then compared with previous expression levels of the same biomarkers in the same subject, with the goal that the subject's expression levels should eventually resemble those of control subjects not at elevated risk of a joint injury. Failure of the expression levels to normalize to levels seen in control subjects can indicate that the treatment of the joint injury is not fully effective, or that further treatment to correct undesirable movement patterns and/or structural abnormalities in the subject should be considered.

The methods of the invention further encompass methods for preventing/reducing the risk of a joint injury in a subject having an elevated risk thereof. The methods include assessing risk of future injury to a joint by comparing expression of one or more biomarkers of cartilage, bone, muscle, ligament, and tendon metabolism in a subject suspected of having an elevated risk of joint injury, with the expression of said same one or more biomarkers in a control subject not suspected of having an elevated risk of joint injury. Said markers may be used alone or in combination with other established methods to assess neuromuscular and biomechanical risk factors for joint injury. Based on this assessment of risk of joint injury, physical therapy or movement retraining interventions are provided to said subject suspected of having an elevated risk of joint injury to correct defects in the movement of joints. Such therapy may be directed to improving range of motion, moderating impact forces exerted during activity, strengthening muscle groups surrounding joints, and improving balance, coordination, and neuromuscular control during dynamic functional movements. These primary prevention programs will focus on improving ankle, knee and hip flexion strength and control, reducing peak vertical and medial ground reaction forces, and limiting excessive high risk frontal plane (e.g., dynamic knee valgus) and transverse plane (e.g., knee internal rotation) movements during jumping, landing, or cutting. Preliminary evidence suggests that these types of exercises may reduce the risk of lower extremity joint injury in high risk populations (10, 38). Biomarkers, alone or in combination with other methods to assess neuromuscular and biomechanical risk factors for joint injury may also be used to assess the effectiveness of these primary intervention programs by monitoring normalization of these indices of high risk movement patterns over time.

The methods discussed herein benefit from use of the kits and diagnostic reagents of the invention to conduct the risk assessment based on biomarker expression. The kits include apparatus for collecting and retaining samples (e.g., syringe, collection cup), apparatus for carrying out testing (e.g., a 96-well plate, 384-well plate, blotting substrates). The apparatus for carrying out testing may be specifically designed, for example, for ELISA testing using antibodies directed to said one or more biomarkers being detected or PCR testing using probes directed to said one or more biomarkers being detected. Each antibody or probe directed to a biomarker being detected is provided as a diagnostic reagent, and multiple diagnostic reagents may be included in a single kit. Labels may be provided separately or included with the antibodies and probes, and the labels may be direct or indirect. A kit may further comprise reagents for use in conducting the testing, as well as one or more control samples. Alternatively, an expression profile for subjects not at elevated risk of joint injury, for use as comparison. Preferably, the expression profile is provided as digital information stored on a computer-readable medium.

Although ELISA is a preferred technique for conducting the assessments of the invention, alternative kits for use in techniques such as immunoblotting nuclease protection assays, in situ hybridization, microarrays, immunohistochemistry, are also envisioned, and appropriate apparatus, and reagents for use in carrying out these well-known techniques may be provided as a part of such a kit.

These and other aspects of the invention are further described in the non-limiting Examples set forth below.

EXAMPLES

Example 1

In order to demonstrate that high risk movement patterns that predispose certain individuals to subsequent ACL injury also influence cartilage turnover and metabolism prior to injury, the association between pre-injury serum levels for biomarkers of cartilage turnover and the subsequent ACL injury was evaluated. In particular, the relationship between pre-injury levels of four serum biomarkers of cartilage turnover and the subsequent likelihood of ACL rupture was studied.

1.1 DESIGN & SETTING

A nested case-control study was conducted to examine the association between pre-injury serum levels of four biomarkers of cartilage turnover and the subsequent risk of ACL injury. The primary outcome of interest was ACL injury case status (ACL injured vs. uninjured control). The independent variables examined included the pre-injury serum concentrations of four biomarkers of cartilage turnover, which included two markers for type II collagen and aggrecan synthesis (CPII and CS846, respectively) and two markers of Types I and II degradation and type II degradation only (C1,2C and C2C, respectively). All subjects were cadets or active duty military personnel at the United States Military Academy (USMA), West Point, N.Y. This study was reviewed and approved by the Institutional Review Board at Keller Army Hospital (West Point, N.Y.) with secondary review from the US Army Clinical Investigation Regulatory Office (Ft. Sam Houston, Tex.).

1.2 CASE SUBJECTS

The ACL injured cases for this study were 45 of 71 subjects from the randomized and non-randomized arms of an existing clinical trial comparing outcomes for ACL reconstructions performed with two different autograft techniques (patellar tendon vs. hamstring tendon) (51). All subjects had confirmed pre-injury serum samples stored in the Department of Defense Serum Repository (DoDSR). Subjects were eligible for inclusion in the clinical trial if they were between the ages of 17 and 45 years and had 1) a history of traumatic incident knee joint injury, 2) symptoms and physical examination findings consistent with the diagnosis of ACL rupture, and 3) MRI findings indicating ACL rupture (51) In all subjects the knee was evaluated arthroscopically to verify the diagnosis of ACL rupture and any concomitant intra-articular injuries to determine eligibility based on the inclusion and exclusion criteria (51). Potential subjects were excluded if they 1) had previously sustained an ACL injury or undergone ACL reconstruction in either knee, 2) sustained multiple knee ligament injuries that required concomitant surgical repair, or 3) presented with a full-thickness chondral lesion (49).

1.3 CONTROL SUBJECTS

A matched control group of 45 healthy subjects with serum samples drawn upon entry to the USMA (baseline pre-injury), following the same timeline as the ACL injured patients with which they were paired, was also studied. The 45 subjects in the matched control group 1) had no history of major joint injury or surgical intervention prior to or during their 4 years at the USMA, 2) met matching criteria for age, sex, height, and weight with a subject in the ACL injured group, and 3) had serum samples in the DODSR for entry to the USMA. The control subjects were drawn from a control pool of 450 potential subjects consisting of 10 possible subjects that matched each ACL injured study subject. The criteria used to match the cases with controls were as follows: same sex, age±2 years, height±2 inches, and weight±15 pounds. Identification of the 10 potential control subjects for each of the 45 ACL injured subjects was performed by the Office of Institutional Research at the USMA.

Following the identification of potential control subjects by the Office of Institutional Research, each potential control subject was screened for a history of major joint injury or surgery prior to and during their four years at the USMA. This was possible because all of the potential control subjects are medically screened prior to entering the USMA and received their healthcare through a closed healthcare system during the four years between the collection of baseline pre-injury samples and graduation 4 years later. Injury surveillance records were reviewed using the Cadet Injury and Illness Tracking System (CIITS), electronic medical records using the Armed Forces Health Longitudinal Technology Application (AHLTA), and surgical records using the Surgery Scheduling System (S3) for each potential control subject. Potential control subjects were excluded if they had a history of major joint injury or surgery prior to or during the four years they were at the USMA. After screening for a history of major joint injury or surgery, the list of remaining eligible control subjects was forwarded to the DODSR. The control subject chosen for each ACL injured study subject was chosen by the DODSR from among the potential controls that met the inclusion criteria based on the availability of entry pre-injury serum samples in the DODSR. The research team was blinded to the identity of the control subjects ultimately selected by the DODSR.

1.4 MEASURES OF CARTILAGE TURNOVER AND METABOLISM

Sera were analyzed using four specific ELISA assays of cartilage turnover: two measuring degradation (C2C and C1,2C) and two measuring synthesis (CS846 and CPII). The assays for CPII, CS846, C1,2C, and C2C are commercially available in 96 well ELISA kits using pre-coated plates from IBEX (Montreal, Quebec, Canada). These biomarkers of type II collagen and aggrecan metabolism were selected for this initial study because type II collagen and aggrecan are the most abundant proteins in articular cartilage. Levels of the procollagen II carboxy propeptide (CP II) has been found to directly correlate with synthesis of type II collagen (35). The aggrecan chondroitin sulfate 846 epitope (CS846) is most concentrated in fetal human cartilage and is almost absent in adult articular cartilage (19). It reappears in osteoarthritic cartilage being present on the largest most intact molecules (43). Furthermore, the CS846 epitope increases markedly in content in joints following injury (28). With regard to collagen degradation, the cleavage of type II collagen by collagenases produces a specific neoepitope at the carboxy terminus of the ¾-length type II collagen cleavage product. A specific assay for collagen type II cleavage (C2C) has been developed and can be used in both serum and synovial fluid (40). Cleavage of types I and II collagen by collagenases can also be detected in a similar fashion using the C1,2C or Col 2 ¾ Short assay (4).

1.5 SPECIMEN ACQUISITION AND TESTING

Federal laws passed in the 1980's directed the Secretary of Defense to establish a system that maintains blood samples in a central location to assess the medical conditions of military service members who deploy outside the United States (1). The DODSR was established to comply with these laws and its purposes include medical surveillance, clinical diagnosis, and epidemiologic studies (45). The DODSR maintains all sera drawn from service members for administrative testing which is required upon initial entry onto any active duty status, prior to commissioning as an officer upon graduation from a service academy or university, and at intervals throughout an individual's time in service. The interval for testing is typically every two years once in the regular military as well as upon deployment and redeployment from overseas assignments. Cadets at the USMA routinely have serum samples drawn upon reception to the Academy and just before graduation four years later prior to being commissioned as officers in the US Army. The primary purpose of the repository is to support force health protection, disease prevention, and public health programs of the military services, particularly related to operational deployments. The DoD encourages military investigators to engage in militarily relevant research which utilizes the resources of the Serum Repository. Because knee joint injuries are endemic in active duty military populations (25, 37) and lead to high rates of osteoarthritis (9, 26) and disability discharge from military service, the DODSR agreed to support this study (14, 46-48). The routine testing of collected serum includes screening for human immunodeficiency virus (HIV), with any samples that remain after testing being maintained within the DODSR for possible future use in support of the public health objectives outlined above. Serum, if available, is released in 0.5 ml volumes except when only the last 0.5 ml remains in the DODSR.

All serum samples for cases and controls in the current study were obtained from the DODSR and were initially aliquoted into separate micro centrifuge tubes and stored at −80° C. until subsequent analyses. Each sample was assayed in triplicate for the four biomarkers of cartilage turnover and metabolism using commercially available pre-coated ELISA kits (IBEX, Inc, Montreal, CA), according to manufacturer guidelines. A Wallac-Victor 1420 (Perkin-Elmer Life Science, Boston, Mass.) multilabel plate reader was used to detect serum absorbances for each cartilage turnover marker at an optical density of 450 nm. Serum concentrations were determined against the known standard curve provided by the manufacturer by utilizing the Workout 2.5 software (Dasdaq Solutions Ltd, East Sussex, England). This process was performed by the same member of the research team who was blinded to the case-control status of each subject. ELISA kits for each biomarker were from the same respective lot numbers to further minimize interassay coefficients of variation (CV). In the current study, intra-assay CVs ranged from 2-4%; inter-assay CVs ranged from 3-9%.

1.6 DATA ANALYSIS

Means and standard deviations for pre-injury baseline serum levels were calculated for all four biomarkers of cartilage turnover and metabolism by group (ACL injured cases and controls). Frequencies, as well as means and standard deviations, were also calculated for other dichotomous and continuous demographic variables of interest, respectively. Initially, independent t-tests and wilcoxon tests were performed to evaluate between group baseline (pre-injury) differences for all markers of interest. Because a matched case-control design was utilized, all biomarkers were subsequently carried forward into conditional logistic regression analyses to evaluate the association between biomarker levels and the subsequent risk of ACL injury. In matched case-control studies, conditional logistic regression accounts for the matching of cases and controls with respect to sex, age, height, and weight, and adjusts for this in the analysis (50). Univariate analyses were first conducted for each biomarker prior to examining several multivariable models to determine the best model for predicting ACL injury status based on the biomarkers that were evaluated. Unadjusted and adjusted odds ratios (OR) and 95% confidence intervals (CI) were calculated for each marker, as well as p-values. Multivariable models were evaluated because some studies have suggested that combinations of biomarkers of cartilage synthesis and degradation may be important in determining changes/differences in cartilage metabolism (5, 8). All statistical analyses were completed using STATA/SE software version 10.1 (StataCorp, College Station, Tex.) and a Type I error rate of $p<0.05$ was used to assess statistical significance.

1.7 RESULTS

Of the 45 ACL injured cases, 39 (86.7%) were males and the remaining 6 (13.3%) were females. Among the male ACL injured cases, the average age was 20.26 (SD=1.29) years, the average height was 179.76 (SD=7.37) cm, and the average weight was 83.99 (SD=12.09) kg. The ACL injured females had an average age, height, and weight of 19.33 (SD=1.03) years, 172.72 (SD=2.78) cm, and 68.33 (SD=6.61) kg, respectively. The mean time from the baseline serum sample until ACL injury was 621 (SD=377) days or ~21 months during follow-up. Based on the matching criteria, the cases and controls were matched for the same sex, age±2 years, height±2 inches, and weight±15 pounds. Baseline samples were also obtained for the uninjured control group and the average time from the baseline sample until the end of follow-up in the control group was 1421 (SD=100) days or ~47 months.

There were significant pre-injury differences in serum biomarker levels of cartilage turnover between the ACL injured cases and the uninjured controls (see FIG. 6). In univariate analyses, both biomarkers for cartilage collagen degradation (C1,2C and C2C) were significantly associated with the subsequent likelihood of ACL injury (see FIG. 7). On average, a 1 nanogram/milliliter (ng/ml) increase in serum C1,2C or C2C levels at baseline was associated with being 9.1 (OR=9.12, 95% CI: 2.55, 32.63) and 4.2 (OR=4.22, 95% CI: 1.70, 10.45) times more likely to sustain a subsequent ACL injury, respectively. Similarly, the biomarkers for cartilage synthesis were also associated with subsequent ACL injury. On average, a 1 ng/ml increase in serum CPII at baseline was associated with being over 19 times more likely (OR=19.43, 95% CI: 3.50, 107.82) to sustain a subsequent ACL injury. In contrast, a 1 ng/ml increase in CS846 at baseline was associated with being 65% less likely (OR=0.35, 95% CI: 0.11, 1.13) to sustain a subsequent ACL injury. The results were similar in multivariable models for C2C, CPII, and CS846; however, after controlling for the influence of the other markers in the model, the association between C1,2C and subsequent ACL injury was no longer significant (see FIG. 2). As a result the biomarker C1,2C was dropped from the final model.

1.8 CONCLUSIONS

Existing pre-injury serum samples stored in the DODSR were utilized to examine the association between serum biomarker levels of cartilage turnover and the subsequent risk of ACL injury. It was surprisingly discovered that the ACL injured cases and uninjured controls matched for sex, age, height, and weight differed significantly in their pre-injury state for all biomarkers studied, with the exception of CS846, which approached significance. These pre-injury differences in serum biomarker levels were also associated with the subsequent risk of ACL injury. Pre-injury baseline differences in serum biomarkers of cartilage turnover have never before been associated with the subsequent risk of ACL injury in a group of young and physically active individuals. These pre-injury differences in cartilage turnover and metabolism may be due to the interaction between unique biomechanical and/or biochemical profiles that place individuals at increased risk for ACL injury. The data also suggest that pre-injury biomechanical profiles may be an important confounding or effect-modifying factor in studying the relationship between biomarkers of cartilage turnover and metabolism and the initiation and progression of post-traumatic osteoarthritis following ACL injury.

Initially, pre-injury differences were noted between ACL injured cases and uninjured controls in a preliminary study that examined changes in biomarker levels of cartilage turnover from the pre-injury state in comparison to the post injury state (32). Pre-injury differences in these markers were unanticipated, as the a priori hypothesis was that there would be no pre-injury group differences, but that differences would emerge following ACL injury between the cases and controls. These findings are significant because pre-injury differences in serum biomarker levels of cartilage turnover suggest that bone and cartilage metabolism in those that go on to tear their ACL may be different when compared to a matched control group with no history of major joint injury. These differences may be reflective of different pre-injury biochemical and/or biomechanical risk profiles that subsequently impact both cartilage metabolism and ACL injury risk.

It will, of course, be appreciated that the above description has been given by way of example only and that modifications in detail may be made within the scope of the present invention.

Throughout this application, various patents and publications have been cited. The disclosures of these patents and publications in their entireties are hereby incorporated by reference into this application, in order to more fully describe the state of the art to which this invention pertains.

The invention is capable of considerable modification, alteration, and equivalents in form and function, as will occur to those ordinarily skilled in the pertinent arts having the benefit of this disclosure.

While the present invention has been described for what are presently considered the preferred embodiments, the invention is not so limited. To the contrary, the invention is intended to cover various modifications and equivalent arrangements included within the spirit and scope of the detailed description provided above.

REFERENCES

1. Guidelines for collecting, maintaining, requesting, and using specimens stored in the Department of Defense Serum Repository: Army Medical Surveillance Activity, Directorate of Epidemiology and Disease Surveillance, U.S. Army Center for Health Promotion and Preventive Medicine; 29 May 2003.

2. Andriacchi T P, Mundermann A. The role of ambulatory mechanics in the initiation and progression of knee osteoarthritis. *Curr Opin Rheumatol.* September 2006; 18(5):514-518.

3. Bauer D C, Hunter D J, Abramson S B, et al. Classification of osteoarthritis biomarkers: a proposed approach. *Osteoarthritis Cartilage.* August 2006; 14(8):723-727.

4. Billinghurst R C, Dahlberg L, Ionescu M, et al. Enhanced cleavage of type II collagen by collagenases in osteoarthritic articular cartilage. *J Clin Invest.* Apr. 1, 1997; 99(7):1534-1545.

5. Birmingham J D, Vilim V, Kraus V B. Collagen biomarkers for arthritis applications. *Biomarker Insights.* 2006; 1:61-76.

6. Boden B P, Sheehan F T, Torg J S, Hewett T E. Noncontact anterior cruciate ligament injuries: mechanisms and risk factors. *J Am Acad Orthop Surg.* September 2010; 18(9): 520-527.

7. Boden B P, Torg J S, Knowles S B, Hewett T E. Video analysis of anterior cruciate ligament injury: abnormalities in hip and ankle kinematics. *Am J Sports Med.* February 2009; 37(2):252-259.

8. Cahue S, Sharma L, Dunlop D, et al. The ratio of type II collagen breakdown to synthesis and its relationship with the progression of knee osteoarthritis. *Osteoarthritis Cartilage.* July 2007; 15(7):819-823.

9. Cameron K L, Hsiao M S, Owens B D, Burks R, Svoboda S J. Incidence of physician diagnosed osteoarthritis among active duty United States military service members. *Arthritis Rheum.* 2011; 63(10):2974-2982.

10. Carow S D, Haniuk E M, Cameron K L, DiStefano L J, Padua D A, Marshall S W, Beutler A I, de la Motte S J, Gerber J P. Risk of lower extremity injury in a military population after performing a supervised injury prevention program. J Athl Train. In press. Accepted for publication 5 Jul. 2013.

11. Chaudhari A M, Andriacchi T P. The mechanical consequences of dynamic frontal plane limb alignment for non-contact ACL injury. *J Biomech.* 2006; 39(2):330-338.

12. DiStefano L J, Blackburn J T, Marshall S W, Guskiewicz K M, Garrett W E, Padua D A. Effects of an age-specific anterior cruciate ligament injury prevention program on lower extremity biomechanics in children. *Am J Sports Med.* May 2011; 39(5):949-957.

13. DiStefano L J, Padua D A, DiStefano M J, Marshall S W. Influence of age, sex, technique, and exercise program on movement patterns after an anterior cruciate ligament injury prevention program in youth soccer players. *Am J Sports Med.* March 2009; 37(3):495-505.

14. Dunn W R, Lincoln A E, Hinton R Y, Smith G S, Amoroso P J. Occupational disability after hospitalization for the treatment of an injury of the anterior cruciate ligament. *J Bone Joint Surg Am.* September 2003; 85-A (9):1656-1666.

15. Englund M. The role of biomechanics in the initiation and progression of OA of the knee. *Best Pract Res Clin Rheumatol.* February 2010; 24(1):39-46.

16. Englund M, Lohmander L S. Risk factors for symptomatic knee osteoarthritis fifteen to twenty-two years after meniscectomy. *Arthritis Rheum.* September 2004; 50(9): 2811-2819.

17. Felson D T. The epidemiology of knee osteoarthritis: results from the Framingham Osteoarthritis Study. *Semin Arthritis Rheum.* December 1990; 20(3 Suppl 1):42-50.

18. Gilchrist J, Mandelbaum B R, Melancon H, et al. A randomized controlled trial to prevent noncontact anterior cruciate ligament injury in female collegiate soccer players. *Am J Sports Med.* August 2008; 36(8):1476-1483.

19. Giant T T, Mikecz K, Roughley P J, Buzas E, Poole A R. Age-related changes in protein-related epitopes of human articular-cartilage proteoglycans. *Biochem J.* May 15, 1986; 236(1):71-75.

20. Harner C D, Paulos L E, Greenwald A E, Rosenberg T D, Cooley V C. Detailed analysis of patients with bilateral anterior cruciate ligament injuries. *Am J Sports Med.* January-February 1994; 22(1):37-43.

21. Hewett T E, Lindenfeld T N, Riccobene J V, Noyes F R. The effect of neuromuscular training on the incidence of knee injury in female athletes. A prospective study. *Am J Sports Med.* November-December 1999; 27(6):699-706.

22. Hewett T E, Myer G D, Ford K R. Reducing knee and anterior cruciate ligament injuries among female athletes: a systematic review of neuromuscular training interventions. *J Knee Surg.* January 2005; 18(1):82-88.

23. Hewett T E, Myer G D, Ford K R, et al. Biomechanical measures of neuromuscular control and valgus loading of the knee predict anterior cruciate ligament injury risk in female athletes: a prospective study. *Am J Sports Med.* April 2005; 33(4):492-501.

24. Hewett T E, Stroupe A L, Nance T A, Noyes F R. Plyometric training in female athletes. Decreased impact forces and increased hamstring torques. *Am J Sports Med.* November-December 1996; 24(6):765-773.

25. Hsiao M, Owens B D, Burks R, Sturdivant R X, Cameron K L. Incidence of acute traumatic patellar dislocation among active-duty United States military service members. *Am J Sports Med.* October 2010; 38(10): 1997-2004.

26. Johnson A E, Cross J D. Impact of traumatic arthritis on a cohort of combat casualties. Paper presented at: American Academy of Orthopaedic Surgeons Annual Meeting; Feb. 8-11, 2011; San Diego, Calif.

27. Lohmander L S, Englund P M, Dahl L L, Roos E M. The long-term consequence of anterior cruciate ligament and meniscus injuries: osteoarthritis. *Am J Sports Med.* October 2007; 35(10):1756-1769.

28. Lohmander L S, Ionescu M, Jugessur H, Poole A R. Changes in joint cartilage aggrecan after knee injury and in osteoarthritis. *Arthritis Rheum.* March 1999; 42(3): 534-544.

29. Lohmander L S, Ostenberg A, Englund M, Roos H. High prevalence of knee osteoarthritis, pain, and functional limitations in female soccer players twelve years after anterior cruciate ligament injury. *Arthritis Rheum.* October 2004; 50(10):3145-3152.

30. Mandelbaum B R, Silvers H J, Watanabe D S, et al. Effectiveness of a neuromuscular and proprioceptive training program in preventing anterior cruciate ligament injuries in female athletes: 2-year follow-up. *Am J Sports Med.* July 2005; 33(7):1003-1010.

31. Markolf K L, Burchfield D M, Shapiro M M, Shepard M F, Finerman G A, Slauterbeck J L. Combined knee loading states that generate high anterior cruciate ligament forces. *J Orthop Res.* November 1995; 13(6):930-935.

32. Meulenbelt I, Kraus V B, Sandell L J, Loughlin J. Summary of the OA biomarkers workshop 2010—genet- 33. Mundermann A, Dyrby C O, Andriacchi T P. Secondary gait changes in patients with medial compartment knee osteoarthritis: increased load at the ankle, knee, and hip during walking. *Arthritis Rheum*. September 2005; 52(9): 2835-2844.
34. Mundermann A, Dyrby C O, Andriacchi T P, King K B. Serum concentration of cartilage oligomeric matrix protein (COMP) is sensitive to physiological cyclic loading in healthy adults. *Osteoarthritis Cartilage*. January 2005; 13(1):34-38.
35. Nelson F, Dahlberg L, Laverty S, et al. Evidence for altered synthesis of type II collagen in patients with osteoarthritis. *J Clin Invest*. Dec. 15, 1998; 102(12):2115-2125.
36. Oliviero F, Ramonda R, Punzi L. New horizons in osteoarthritis. *Swiss Med Wkly*. 2010; 140:w13098.
37. Owens B D, Mountcastle S B, Dunn W R, DeBerardino T M, Taylor D C. Incidence of anterior cruciate ligament injury among active duty U.S. military servicemen and servicewomen. *Mil Med*. January 2007; 172(1):90-91.
38. Owens B D, Cameron K L, Duffey M L, Vargas D, Duffey M J, Mountcastle S B, Padua D A, Nelson B J. Military movement training program improves jump landing mechanics associated with ACL injury risk. J Surg Orthop Advances. 2013; 22(1): 66-70.
39. Padua D A, DiStefano L J. Sagital plane knee biomechanics and vertical ground reaction forces are modified following ACL injury prevention programs: A systematic review. *Sports Health*. 2009; 1(2):165-173.
40. Poole A R, Ionescu M, Fitzcharles M A, Billinghurst R C. The assessment of cartilage degradation in vivo: Development of an immunoassay for the measurement in body fluids of type II collagen cleaved by collagenases. *J Immunological Methods*. 2004; 294:145-153.
41. Posthumus M, September A V, Keegan M, et al. Genetic risk factors for anterior cruciate ligament ruptures: COL1A1 gene variant. *Br J Sports Med*. May 2009; 43(5):352-356.
42. Posthumus M, September A V, O'Cuinneagain D, van der Merwe W, Schwellnus M P, Collins M. The COL5A1 gene is associated with increased risk of anterior cruciate ligament ruptures in female participants. *Am J Sports Med*. November 2009; 37(11):2234-2240.
43. Rizkalla G, Reiner A, Bogoch E, Poole A R. Studies of the articular cartilage proteoglycan aggrecan in health and osteoarthritis. Evidence for molecular heterogeneity and extensive molecular changes in disease. *J Clin Invest*. December 1992; 90(6):2268-2277.
44. Roos E M. Joint injury causes knee osteoarthritis in young adults. *Curr Opin Rheumatol*. March 2005; 17(2): 195-200.
45. Rubertone M V, Brundage J F. The Defense Medical Surveillance System and the Department of Defense serum repository: glimpses of the future of public health surveillance. *Am J Public Health*. December 2002; 92(12): 1900-1904.
46. Songer T J, LaPorte R E. Disabilities due to injury in the military. *Am J Prev Med*. April 2000; 18(3 Suppl):33-40.
47. Sulsky S I, Mundt K A, Bigelow C, Amoroso P J. Case-control study of discharge from the U.S. Army for disabling occupational knee injury: the role of gender, race/ethnicity, and age. *Am J Prev Med*. April 2000; 18(3 Suppl):103-111.
48. Sulsky S I, Mundt K A, Bigelow C, Amoroso P J. Risk factors for occupational knee related disability among enlisted women in the U S Army. *Occup Environ Med*. September 2002; 59(9):601-607.
49. Svoboda S J, Harvey T, Owens B D, Tarwater P, Brechue W, Cameron K L. Changes in serum biomarkers of cartilage turnover following ACL reconstruction. Paper presented at: American Orthopaedic Society for Sports Medicine Annual Meeting; 7-9 Jul. 2011; San Diego, Calif.
50. Szklo M, Nieto F J. Stratification and adjustment: Multivariate analysis in epidemiology. *Epidemiology Beyond the Basics*. 2nd ed. Salsbury, M A: Jones and Bartlett; 2007:227-295.
51. Taylor D C, DeBerardino T M, Nelson B J, et al. Patellar tendon versus hamstring tendon autografts for anterior cruciate ligament reconstruction: a randomized controlled trial using similar femoral and tibial fixation methods. *Am J Sports Med*. October 2009; 37(10):1946-1957.

What is claimed:

1. A method for diagnosing and reducing an elevated risk of an ACL injury in a human, comprising:
    (a) measuring the expression level of one or more biomarkers of cartilage metabolism in a sample taken from the human, wherein said one or more biomarkers are C1,2C, C2C, CPII, and/or CS846;
    (b) comparing the expression level of the one or more biomarkers in the sample with the expression level of the same one or more biomarkers in a normal control;
    (c) determining that the human has an elevated risk of future ACL injury based on an increased expression level of one or more of C1,2C, C2C, or CPII in the sample compared to the normal control, or a decreased expression level of CS846 in the sample compared to the normal control, or a combination thereof; and
    (d) administering an ACL-injury reducing intervention to the human to reduce the elevated risk of future ACL injury, wherein the intervention is physical therapy, movement retraining, surgery, or pharmaceutical therapy.

2. The method of claim 1, wherein said human has an increased expression level of C1,2C and a decreased level of CS846 compared to the normal control.

3. The method of claim 1, wherein said human has an increased expression level of C2C and CPII compared to the normal control.

4. The method of claim 1, wherein said human has an increased expression level of C2C and a decreased level of CS846 compared to the normal control.

5. The method of claim 1, wherein said human has an increased expression level of CPII and a decreased level of CS846 compared to the normal control.

6. The method of claim 1, wherein said human has an increased expression level of C1,2C, C2C and CPII compared to the normal control.

7. The method of claim 1, wherein said human has an increased expression level of C2C and CPII compared to a control, and a decreased expression level of CS846 compared to the normal control.

8. The method of claim 1, wherein said human has an increased expression level of C1,2C, C2C and CPII, and a decreased expression level of CS846 compared to the normal control.

9. The method of claim 1, wherein the human has an increased expression level of C1,2C and C2C compared to the normal control.

10. The method of claim 1, wherein the human has an increased expression level of C1,2C and CPII compared to the normal control.

11. The method of claim 1, further comprising determining expression levels of biomarkers of bone metabolism, biomarkers of muscle metabolism, biomarkers of ligament metabolism, and/or biomarkers of tendon metabolism.

12. The method of claim 11, wherein the one or more biomarkers are CTX-II, COMP, HA, Coll2-1 and Coll2-1, NO2, PHANP, NTX-1, CTX-1, MMP-3, MMP1, MMP2, MMP7-MMP28, VEGF, PDGF, IGF-1, IGF-2, CRP, ESR, and/or Vitamin D.

13. The method of claim 1, further comprising determining whether the human has an elevated risk of ACL injury based on biomechanical assessment of the joint.

14. The method of claim 1, wherein the ACL injury is a tear.

\* \* \* \* \*